United States Patent [19]
Larson

[11] Patent Number: 4,893,406
[45] Date of Patent: Jan. 16, 1990

[54] EXTENSION APPARATUS FOR TOENAIL CLIPPERS

[76] Inventor: James D. Larson, P.O. Box 972, Vashon, Wash. 98070

[21] Appl. No.: 256,529

[22] Filed: Oct. 12, 1988

[51] Int. Cl.$^4$ ............................................. A45D 29/02
[52] U.S. Cl. .......................................... 30/28; 30/177; 30/184; 30/297
[58] Field of Search ...................... 30/26, 28, 145, 175, 30/176, 177, 184, 241, 242, 296 R, 231, 29, 297; 128/80 B

[56] References Cited

U.S. PATENT DOCUMENTS

| | | | |
|---|---|---|---|
| 857,790 | 6/1907 | Carroll | 30/29 |
| 1,449,165 | 3/1923 | Cameron | 30/123 R |
| 1,579,783 | 4/1926 | Ross | 30/296 |
| 1,721,415 | 7/1929 | Schnefel | 30/28 |
| 2,460,522 | 2/1949 | Miller | 30/28 |
| 2,615,242 | 10/1952 | Franklin | 30/28 |
| 4,241,499 | 12/1980 | Perrone | 30/27 |

FOREIGN PATENT DOCUMENTS

| | | | |
|---|---|---|---|
| 959853 | 3/1957 | Fed. Rep. of Germany | 30/28 |
| 2154872 | 9/1985 | United Kingdom | 132/73.5 |

Primary Examiner—Frank T. Yost
Assistant Examiner—Y. Lin
Attorney, Agent, or Firm—Henderson & Sturm

[57] ABSTRACT

An extension apparatus (10) in combination with a conventional nail clipping device (100); wherein, the extension apparatus comprises an elongated extension member (13) and a remote actuating unit (12) which are operatively connected to the conventional nail clipping device (100), and wherein the extension member (13) is further provided with a visual inspection member (50) and a support member (40).

2 Claims, 1 Drawing Sheet

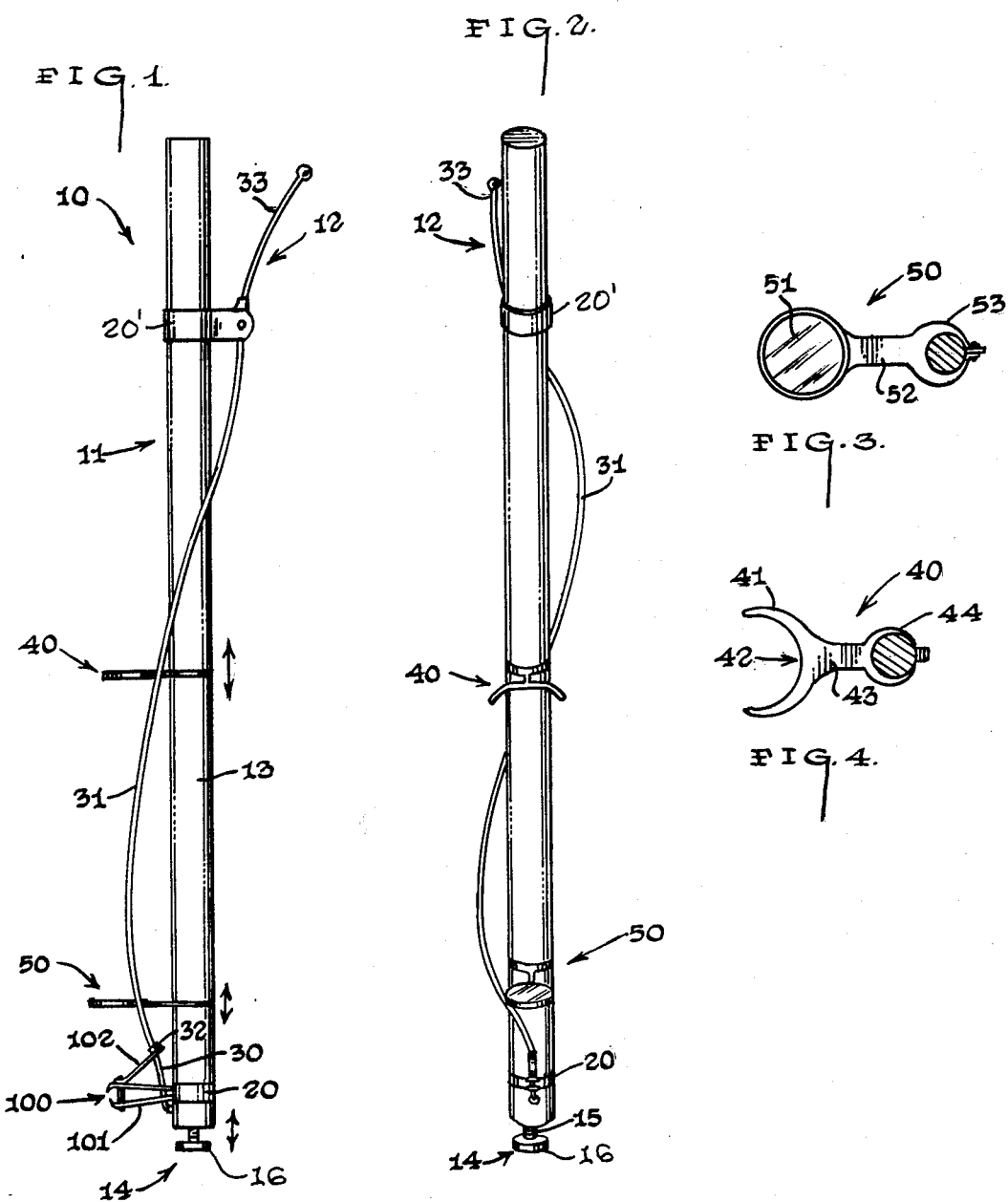

EXTENSION APPARATUS FOR TOENAIL CLIPPERS

TECHNICAL FIELD

This invention relates to the field of nail clipping apparatus in general, and more specifically to an extension apparatus that will permit the remote actuation of a conventional nail clipping device.

BACKGROUND OF THE INVENTION

As can be seen by reference to the following U.S. Pat. Nos.: 4,241,499; 1,721,415; 2,615,242; and 2,460,522 the prior art is replete with myriad and diverse nail clipping devices.

However, for many individuals the relatively simple task of cutting one's own toenails with a nail clipper becomes a herculean if not impossible task due to age, infirmity, and/or obesity; wherein, the particular individual is incapable of easily reaching their toes with a nail clipping device.

While all of the aforementioned prior art constructions are more than adequate for the purpose of effecting the basic nail clipping function when the user is capable of positioning the nail clipping apparatus in an unaided fashion proximate the toenails, none of these above mentioned patent constructions are designed to be actuated from a remote location when the user is incapable of affecting the required pre-positioning of the clipping apparatus.

Obviously, there has existed a longstanding need among those individuals who lack the mobility required to manually position the nail clipping device in contact with their toenails for an extension apparatus that will permit both the remote positioning and actuation of the clipping device at the desired location, and the present invention was specifically developed to satisfy that need.

BRIEF SUMMARY OF THE INVENTION

Briefly stated, the present invention involves an extension apparatus for nail clippers, wherein the extension apparatus comprises in general: an extension unit, and a remote actuation unit which are operatively associated with a conventional nail clipping device, whereby, the nail clipping device may be positioned and actuated from a remote location.

In addition, the extension apparatus of this invention further contemplates the provision of an adjustment means associated with the extension unit to vary the location of the nail clipping device relative to a floor surface.

Furthermore, the extension apparatus of this invention also contemplates the use of visual inspection and support means in conjunction with the extension unit; whereby, the user will be able to support and stabilize the position of the nail clipper relative to their toenails, and will also be able to visually observe in magnified fashion the positioning of the nail clipper jaws relative to their toenails.

BRIEF DESCRIPTION OF THE DRAWINGS

These and other objects, advantages, and novel features of the invention will become apparent from the detailed description of the best mode for carrying out the preferred embodiment of this invention which follows, particularly when considered in conjunction with the accompanying drawings, wherein:

FIG. 1 is a side plan view of the extension apparatus of this invention equipped with a convention nail clipping device;

FIG. 2 is a perspective view of the extension apparatus and nail clipping device;

FIG. 3 is an enlarged top plan view of the visual inspection means; and,

FIG. 4 is an enlarged top plan view of the support means.

BEST MODE FOR CARRYING OUT THE INVENTION

As can be seen by reference to the drawings and in particular to FIG. 1, the extension apparatus that forms the basis of the present invention is designated generally by the reference numeral (10). The extension apparatus (10) is designed to be used in conjunction with a conventional nail clipping device (100) and comprises in general: an extension unit (11) and a remote actuating unit (12), both of which are operatively connected to the nail clipping device (100). These units will now be described in seriatim fashion.

As shown in FIGS. 1 and 2, the extension unit (11) comprises an elongated generally tubular extension member (13) having an adjustment means (14) disposed on its lower end, which will incrementally vary the effective length of the extension member (13) in a well recognized fashion. In the preferred embodiment of this invention depicted in the drawings, the adjustment means (14) comprises an elongated threaded member (15) which engages a complementary threaded aperture (not shown) in the extension member (13); and the adjustment means (14) is further provided with an enlarged head portion (16), which serves as the base of the extension member (13). However, it should also be noted that any suitable adjustment means (14) may be substituted therefore in keeping with the teachings of this invention.

As can also be seen by reference to FIGS. 1 and 2, the conventional nail clipping device (100) is secured to the lower portion of the elongated generally tubular extension member (13) by a suitable clamp means (20) which will dispose the nail clipping device (100) generally perpendicular to the longitudinal axis of the elongated tubular extension member (13); wherein, the conventional nail clipping device (100) comprises in general: a pair of jaw members (101) mounted for relative reciprocation with respect to one another; wherein, the actuation of the jaw members (101) is controlled by an actuating lever (102).

As can also be seen by reference to FIGS. 1 and 2, the remote actuating unit (12) comprises an elongated spring loaded cable element (30) which is contained with in a flexible sheath element (31); wherein, the lower end of the cable element (30) is provided with an enlarged collar member (32), whose position relative to the lower end of the sheath element (31) is controlled by an actuating handle member (33) which is operatively secured to the upper portion of the remote actuating unit (12).

In the embodiment depicted in the drawings, the remote actuating unit (12) consists of a well recognized cable actuator similar to those employed to actuate bicycle brakes; however, this invention also contemplates the user of a plunger actuated remote actuating unit (not shown), or any suitable remote actuating device that would be capable of transmitting a downwardly directed force on the nail clipping device actuating lever (102).

As is best depicted in FIG. 1, the remote actuating unit (12) is disposed on the upper portion of the elongated tubular extension member (13) by means of a suitable clamp means (20'); wherein, the enlarged collar member (32) of the cable element (30) operatively engages the actuating lever (102) of the nail clipping device (100) for the purpose of selectively applying a downwardly directed force thereon through the actuating handle member (33) of the remote actuating unit (12).

As shown in FIGS. 1 and 2, the extension apparatus (10) of this invention also contemplates the provision of a support member (40) and a visual inspection member (50) on the elongated tubular extension member (13) intermediate the location of the clipping device (100) and the actuating handle member (33) of the remote actuating unit (12).

As can best be seen by reference to FIGS. 1 thru 3, the support member (40) comprises a leg brace element (41) having a generally C-shaped brace portion (42) disposed on the outboard end of a stem member (43) whose inboard end is provided with a clamp element (44) adapted to engage the periphery of the elongated extension member (13) in a well recognized fashion. The leg brace element (41) is employed to provide a resting surface for the apparatus (10) whereby the apparatus may be stabilized by contact with the users leg.

As can best be seen by reference to FIGS. 1, 2, and 4, the visual inspection member (50) comprises a magnifying glass element (51) which is mounted on the outboard end of a stem member (52) whose inboard end is provided with a clamp element (53) adapted to engage the periphery of the elongated extension member (13). The magnifying glass element (51) is provided so that the user will have a magnified view of the engagement between the jaws (101) of the nail clipping device (100) and the users toenails (not shown).

It should also be appreciated at this juncture that both the support member (40) and the visual inspection member (50) are adapted to be selectively positioned along the axial length of the elongated extension member (13); and, that if desired both the support (40) and visual inspection (50) members may be provided with suitable locking mechanisms (60) if so desired on their respective clamp elements (44) and (53).

Having thereby described the subject matter of this invention it should be apparent that many substitutions, modifications, and variations of the invention are possible in light of the above teachings. It is therefore to be understood that the invention as taught and described herein is only to be limited to the extent of the breadth and scope of the appended claims.

What is claimed:

1. The combination of a conventional nail clipping device having a pair of jaw members mounted for relative reciprocation with respect to one another by virtue of the movement of an actuating lever, and an extension apparatus wherein the extension apparatus consists of:

an extension unit comprising an elongated extension member having the conventional nail clipping device operatively secured on the lower portion of the elongated extension member and disposed in a generally perpendicular fashion to the longitudinal axis of said elongated extension member;

a remote actuating unit comprising an elongated spring loaded cable element which is contained in a flexible sheath element wherein the spring loaded cable element is operatively secured on one end to the actuating lever of said conventional nail clipping device for the purpose of exerting a downwardly directed force thereon; wherein, the other end of said remote actuating unit is operatively connected to the upper portion of the elongated extension member;

a visual inspection member operatively associated with the extension unit wherein the visual inspection member comprises a magnifying glass element which is operatively secured to said elongated extension member above the location of said conventional nail clipping device; and, a support member operatively associated with the extension unit wherein the support member comprises a leg brace element which is disposed above the location of both the conventional nail clipping device and the visual inspection member; and, wherein both the leg brace element and the visual inspection member are movably disposed relative to the longitudinal axis of said extension member.

2. The combination of claim 1 wherein the extension unit is further provided with an adjustment means that is adapted to incrementally vary the effective length of said elongated extension member.

* * * * *